United States Patent [19]

Chikama

[11] Patent Number: 5,167,221
[45] Date of Patent: Dec. 1, 1992

[54] BENDING DEVICE

[75] Inventor: Toshio Chikama, Tokyo, Japan

[73] Assignee: Kabushiki Kaisha Machida Seisakusho, Tokyo, Japan

[21] Appl. No.: 669,729

[22] Filed: Mar. 14, 1991

[30] Foreign Application Priority Data

Mar. 14, 1990 [JP] Japan .................... 2-61200

[51] Int. Cl.⁵ .............................. A61B 1/00
[52] U.S. Cl. ............................................ 128/4
[58] Field of Search .................... 128/4; 604/95

[56] References Cited

U.S. PATENT DOCUMENTS

| 3,470,876 | 10/1969 | Barchilon | 128/4 |
| 3,892,228 | 7/1975 | Mitsui | 128/4 |
| 4,294,233 | 10/1981 | Takahashi | 128/4 |
| 4,329,980 | 5/1982 | Terada . | |
| 4,688,555 | 8/1987 | Wardle | 128/4 |
| 4,841,950 | 6/1989 | Fukuda . | |
| 4,996,974 | 3/1991 | Ciarlei | 128/4 |

FOREIGN PATENT DOCUMENTS 2747653 3/1978 Fed. Rep. of Germany .
2752325 6/1978 Fed. Rep. of Germany .
52-144178 12/1977 Japan .
56-12132 3/1981 Japan .
57-14184 3/1982 Japan .
59-57905 4/1984 Japan .
63-130037 6/1988 Japan .

Primary Examiner—Richard J. Apley
Assistant Examiner—Karen Ann Richard
Attorney, Agent, or Firm—Fish & Richardson

[57] ABSTRACT

There is disclosed a bending device for use in an endoscope or the like. A rear end portion of an insertion tube is supported on a front portion of the body for movement relative thereto along the axis of the insertion tube. The tension of a wire is adjusted by adjusting the position of the insertion tube in its axial direction. A fixing member releaseably fixes the rear end portion of the insertion tube to the front portion of the body at a desired position within a predetermined range of the axial movement of the insertion tube. A rear end of a guide tube guiding the wire therethrough is retained by the rear end portion of the insertion tube, and is moved together with the rear end portion of the insertion tube during the above adjustment of the position of the insertion tube.

10 Claims, 2 Drawing Sheets

BENDING DEVICE

BACKGROUND OF THE INVENTION

This invention relates to a bending device for use in an endoscope or the like.

Generally, an endoscope comprises a hollow body, an insertion tube extending from the front end of the body, a bending tube extending from the front end of the insertion tube, an operating mechanism mounted on the body so as to bend the bending tube in a remotely controlled manner, and one or more wires for transmitting an operating force of the operating mechanism to the bending tube. The operating mechanism, for example, comprises a manipulation knob mounted outside the body, a pulley mounted within the body, and a shaft extending through the side wall of the body and interconnecting the manipulation knob and the pulley. The wire is passed through the bending tube and the insertion tube, and is fixedly secured at its front end to the front end of the bending tube and also is fixedly secured at its rear end to the pulley of the operating mechanism. When the manipulation knob of the operating mechanism is rotated to pull the wire, the bending tube is bent.

The tension of the wire greatly influences the bending operation. More specifically, if the tension of the wire is weak, a play develops in the operation of the manipulation knob. In this condition, in order to bend the bending tube to a desired angle, the manipulation knob needs to be angularly moved to a large extent. In contrast, if the tension of the wire is strong, a large operating force is required, and also the insertion tube and the bending tube are subjected to meandering or torsion, so that the bending tube can not be bent to a desired angle by the operating mechanism.

Japanese Laid-Open (Kokai) Patent Application No. 144178/77 discloses an endoscope in which spring-loaded moving pieces mounted within a body are pressed against a wire so as to always keep the wire taut under a constant tension. In this endoscope, the moving pieces and a spring must be accommodated within the body, which results in an increased size of the body. Further, when the wire is stretched or becomes longer after a long-term use of the endoscope, the amount of deformation of that portion of the wire on which the moving piece acts is increased, so that the resilient force applied by the spring to the wire is weakened. Still further, the resilient force applied to the wire may be weakened because of deterioration of the spring. In these cases, in order to readjust the tension of the wire, the body must be disassembled for the purpose of exchanging the spring. This is a cumbersome operation.

In an endoscope disclosed in Japanese Patent Publication No. 12132/81, an operating mechanism is movable relative to a body in a longitudinal direction of an insertion tube. More specifically, a rectangular slot extending in the direction of the axis of the insertion tube is formed through the side wall of the body. The operating mechanism includes a pair of plates disposed respectively inside and outside the body. The pair of plates are slidable relative to a pair of opposed edges of the slot so as to adjust the position of the operating mechanism, thereby adjusting the tension of a wire. After this position adjustment is finished, the pair of plates are moved toward each other to clamp the side wall of the body therebetween, thereby preventing the operating mechanism from movement relative to the body. This endoscope is complicated in construction, and it is difficult for this endoscope to have a waterproof construction.

Japanese Patent Publication No. 14184/82 discloses an endoscope similar to that disclosed in Japanese Patent Publication No. 12132/81. An operating mechanism of this endoscope has one slide plate. The slide plate is guided by a guide plate mounted in a slot in a body, and is slidable so as to adjust the position of a operating mechanism in the axial direction of the insertion tube. A pin of the operating mechanism is engaged in one of teeth of the guide plate to thereby prevent the operating mechanism from movement relative to the body in the direction of the axis of the insertion tube. This endoscope also has disadvantages similar to those mentioned above with respect to Japanese Patent Publication No. 12132/81.

Japanese Laid-Open Patent Application No. 130037/88 describes in FIGS. 3 and 7 a connecting member which interconnects a body and an insertion tube. The rear end portion of the insertion tube is secured to the front portion of the connecting member. The rear portion of the connecting member is fixed to the body. Therefore, the position of the connecting member relative to the body and hence the position of the insertion tube relative to the body can not be adjusted.

Japanese Laid-Open Utility Model Application No. 57905/84 describes in FIG. 2 a connecting member which interconnects a body and a flexible tube. This connecting member is fixed at a predetermined position relative to the body. Also, in FIGS. 2 and 7 of this prior application, there is shown a retaining member which retains a rear end of a flexible guide tube through which a wire is passed. This retaining member is not fixed to a connecting member, and is fixed to a frame of the body.

SUMMARY OF THE INVENTION

It is an object of this invention to provide a bending device which can easily adjust the tension of a wire, and is simple in construction.

According to the present invention, there is provided a bending device comprising:

(a) a body;

(b) insertion tube means extending from a front end of the body, a rear end portion of the insertion tube means being supported on a front portion of the body for movement relative thereto along an axis of the insertion tube means;

(c) fixing means for releaseably fixing the rear end portion of the insertion tube means to the front portion of the body at a desired position within a predetermined range of axial movement of the insertion tube means;

(d) a bending tube extending from a front end of the insertion tube means;

(e) operating means mounted on the body so as to bend the bending tube in a remotely controlled manner;

(f) a wire passing through the bending tube and the insertion tube means, the wire being connected at one end thereof to a front end of the bending tube and connected at the other end thereof to the operating means so as to transmit an operating force of the operating means to the bending tube; and (g) a guide tube guiding the wire therethrough, a front end of the guide tube being secured to a rear end of the bending tube, a rear end of the guide tube being retained by the rear end portion of the insertion tube means.

DESCRIPTION OF THE PREFERRED EMBODIMENTS OF THE INVENTION

Figure 1:
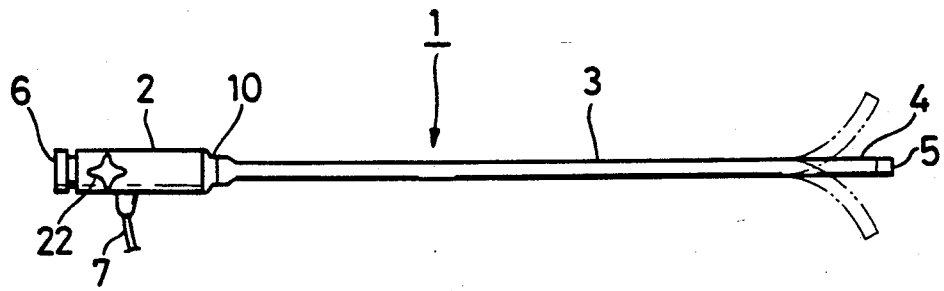
FIG. 1 is a schematic front-elevational view of an endoscope incorporating a bending device according to the present invention.

One preferred embodiment of the invention will now be described with reference to FIGS. 1 to 3. As shown in FIG. 1, an endoscope 1 comprises a hollow cylindrical body 2, a flexible insertion tube 3 extending from the front end of the body 2, a bending tube 4 extending from the front end of the insertion tube 3, and a rigid tip 5 mounted on the front end of the bending tube 4. The body 2 has a uniform transverse cross-section througout the entire length thereof. An ocular tube 6 is mounted on the rear end of the body 2. An inspection window and an illumination window are formed on the front end face of the tip 5. The inspection window is optically connected to the ocular tube 6 by an image-transmitting optical system (not shown) including an optical fiber bundle. A tube 7 extends from the side wall of the body 2. The illumination window is optically connected to a light source via another optical fiber bundle. This optical fiber bundle is optically connected at its one end to the light source, and is passed through the tube 7, the body 2, the insertion tube 3 and the bending tube 4, and is optically connected at the other end thereof to the illumination window.

Figure 2:
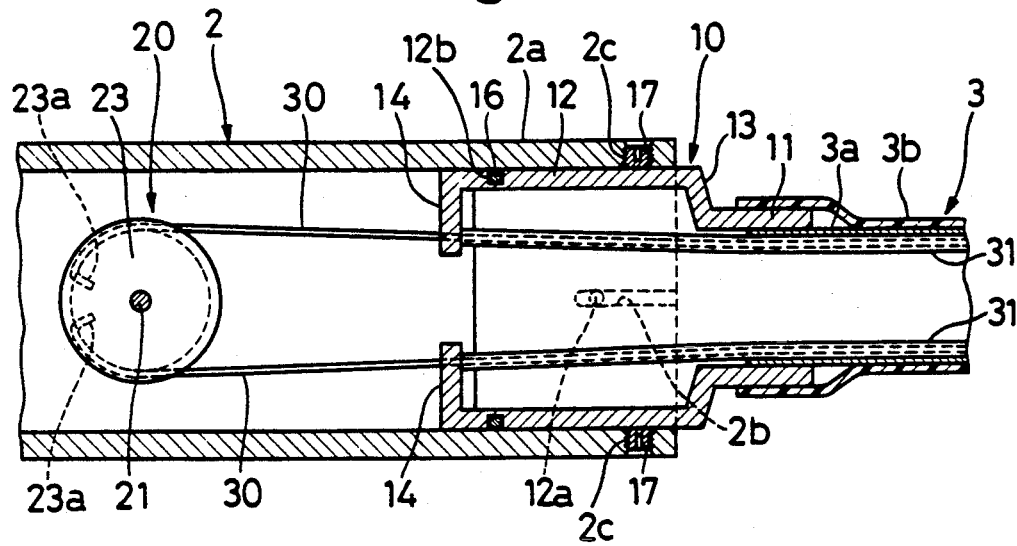
FIG. 2 is a cross-sectional view of an important portion of the endoscope, showing a mechanism for adjusting the tension of wires.

As shown in FIG. 2, the insertion tube 3 is of a conventional construction, and more specifically comprises an inner layer 3a consisting of a spirally-wound metal strip and a braid fitted thereon, and an outer layer 3b of a resin. The bending tube is also of a conventional construction, and therefore explanation thereof is omitted.

The proximal or rear end portion of the insertion tube 3 is connected to the body 2 through a rigid connecting member 10. More specifically, the connecting member 10 includes a cylindrical front portion 11 of a smaller diameter, a cylindrical rear portion 12 of a greater diameter, a step or shoulder portion 13 interconnecting the front and rear portions 11 and 12, and a pair of end walls 14 extending radially inwardly from the rear end of the connecting member 10 in radially opposed relation to each other. The rear end portion of the inner layer 3a of the insertion tube 3 is fitted in and fixed to the inner peripheral surface of the front portion 11 of the connecting member 10. The rear end portion of the outer layer 3b of the insertion tube 3 is fitted on and fixed to the outer peripheral surface of the front portion 11 of the connecting member 10. Thus, the front portion 11 of the connecting member 10 serves as a mounting portion on which the rear end portion of the insertion tube 3 is mounted.

The rear portion 12 of the connecting member 10 is inserted in a front portion 2a of the body 2. Since the outer diameter of the rear portion 12 of the connecting member 10 is substantially equal to the inner diameter of the front portion 2a of the body 2, there is no radial play between the two. The rear portion 12 of the connecting member 10, like the front portion 2a of the body 2, has a uniform cross-section over the entire length thereof, and therefore the rear portion 12 is slidable relative to the front portion 2a of the body 2 in the direction of the axis of the body 2. Thus, the rear portion 12 of the connecting member 10 serves as a slide portion, and the front portion 2a of the body 2 serves as a guide portion for the connecting member 10.

Figure 3:
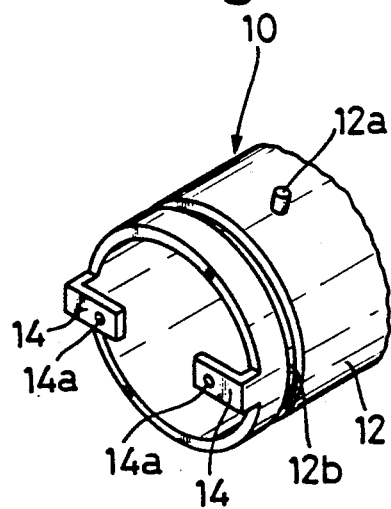
FIG. 3 is a perspective view of an end portion of a connecting member.

As shown in FIGS. 2 and 3, a pin-like projection 12a is formed on and extends radially outwardly from the outer periphery of the rear portion 12 of the connecting member 10. A slot 2b is formed in the body 2 and extends a predetermined distance from the front end of the body 2 in the direction of the axis of the body 2. The projection 12a is received in the slot 2b for movement therealong. With this arrangement, the connecting member 10 is allowed to move relative to the body 2 only in its axial direction, but is prevented from angular movement relative to the body 2.

An annular groove 12b is formed in the outer peripheral surface of the rear portion 12 of the connecting member 10. A seal ring 16 is received in the annular groove 12b to form a seal between the rear portion 12 of the connecting member 10 and the front portion 2a of the body 2.

Screw holes 2c are formed radially through the peripheral wall of the front portion 2a of the body 2. Fixing screws 17 are threaded into the screw holes 2c, respectively. When the inner ends of the fixing screws 17 are firmly held against the outer peripheral surface of the rear portion 12 of the connecting member 10, the connecting member 10 is prevented from sliding movement relative to the body 2 in the direction of the axis of the body 2.

The pair of end walls 14 of the connecting member 10 serve as retaining means for retaining rear ends of a pair of guide tubes 31 (later described), respectively. Each of the end walls 14 has a through hole 14a extending in the direction of the axis of the connecting member 10, and wires 30 (later described) are passed through these through holes 14a, respectively. The diameter of the through hole 14a is greater than the diameter of the wire 30, and is smaller than the outer diameter of the guide tube 31.

An operating mechanism 20 for operating or bending the bending tube 4 is mounted on the body 2. More specifically, the operating mechanism 20 comprises a shaft 21 extending through the peripheral wall of the body 2, a manipulation knob 22 fixedly mounted on one end of the shaft 21 disposed exteriorly of the body 2, and a pulley 23 fixedly mounted on the other end of the shaft 21 disposed within the body 2.

The pulley 23 is connected to the bending tube 4 through the pair of wires 30. More specifically, the rear ends of the pair of wires 30 are respectively inserted in and fixed to a pair of holes 23a formed in the outer peripheral surface of the pulley 23, and the pair of wires 30 extend respectively from the opposite sides of the periphery of the pulley 23 toward the insertion tube 3, and are passed through the insertion tube 3 and the bending tube 4, and are connected at their front ends to the tip 5 in radially spaced relation to each other.

Within the body 2, the pair of wires 30 are passed respectively through the pair of through holes 14a formed respectively through the pair of end walls 14 formed on the rear end of the connecting member 10.

At the insertion tube 3, the pair of wires 30 are passed respectively through the pair of flexible guide tubes 31. The guide tube 31 is formed by spirally winding a metal wire tightly. The front ends of the pair of guide tubes 31 are fixedly secured to a connecting tube (not shown) interconnecting the insertion tube 3 and the bending tube 4, and are disposed in radially opposed relation to each other at the boundary between the insertion tube 3 and the bending tube 4. The rear ends of the pair of guide tubes 31 are held against the pair of end walls 14 of the connecting member 10, respectively.

In the endoscope 1 of the above construction, when the manipulation knob 22 is rotated in a clockwise direction (FIGS. 1 and 2), the pulley 23 is rotated in the same direction, so that the lower wire 30 is pulled whereas the upper wire 30 is loosened. As a result, the bending tube 4 is bent downward. In contrast, when the manipulation knob is rotated in a counterclockwise direction, the bending tube 4 is bent upward.

The front end of each guide tube 31 is fixed to the front end of the insertion tube 3, that is, to the rear end of the bending tube 4, and the rear end of the guide tube 31 is abutted against the end wall 14 of the connecting member 10. Therefore, the length of the guide tube 31 within the insertion tube 3 is not changed, and this prevents the length of the wire 30 within the insertion tube 3 from being changed. Therefore, when the operating force of the manipulating knob 22 is converted into a pulling force to pull the wire 31, this pulling force efficiently acts to bend the bending tube 4, and will not cause meandering of the insertion tube 3.

After the endoscope 1 of the above construction is assembled, the tension of the wires 30 is adjusted before shipment as follows. The manipulation knob 22 is actually angularly moved to pull the wire 30 to bend the bending tube 4. At this time, if there is a play in such pulling, or if the degree of bending of the bending tube 4 is small as compared with the amount of angular movement of the manipulation knob 22, the fixing screws 17 are loosened, and then the connecting member 10 is slidingly moved in a direction away from the rear end of the body 2. As a result, the insertion tube 3 and the bending tube 4 are moved away from the body 2, so that the wires 30 are made taut. Then, the fixing screws 17 are again threaded into the respective screw holes 2c to fix the connecting member 10 to the body 2. In contrast, if the tension of the wires 30 are excessive, the operating force required becomes large, and also the insertion tube 3 and the bending tube 4 are subjected to meandering even in an inoperative condition of the manipulation knob 22. In this case, the fixing screws 17 are loosened, and then the connecting member 10 is moved toward the rear end of the body 2 to reduce the tension of the wires 30. Then, the fixing screws 17 are tightened to fix the connecting member 10 to the body 2. In this manner, the wires 30 can be adjusted to the optimum tension, and this adjustment operation can be carried out easily. And besides, this adjustment operation will not adversely affect the sealing effect of the seal ring 16.

In the endoscope 1 of the above construction, when the wires 30 are stretched or become longer after a long-term use, the tension of the wires 30 can be easily re-adjusted in the above manner without disassembling the body 2.

During the time when the position of the connecting member 10 and the insertion tube 3 is adjusted relative to the body 2 in the axial direction, the end walls 14 of the connecting member 10 are moved together with the insertion tube 3. Therefore, it is ensured that the rear ends of the guide tubes 31 are kept retained by the end walls 14 of the connecting member 10, respectively.

During the time when the position of the connecting member 10 and the insertion tube 3 is adjusted relative to the body 2 in the axial direction, the angular movement of the connecting member 10 and the insertion tube 3 relative to the body 2 is prevented by the engagement of the projection 12a of the connecting member 10 in the slot 2b in the body 2. Therefore, the contents of the insertion tube 3, including the wires 30, the optical fiber bundles and etc., are prevented from being twisted.

Figure 4:
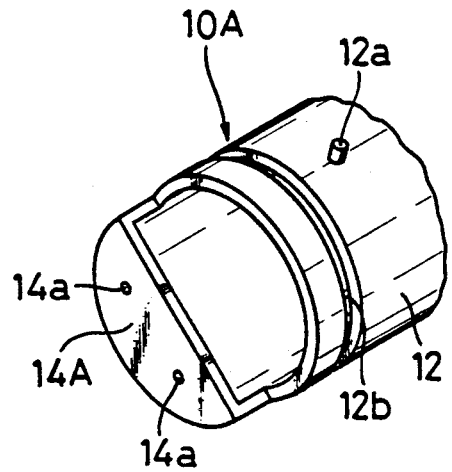
FIG. 4 is a view similar to FIG. 3, but showing a modified connecting member.

FIG. 4 shows a modified connecting member 10A. The connecting member 10A has an end wall 14A of a semi-circular shape formed at its rear end. The end wall 14A serves as retaining means for retaining the guide tubes. A pair of through holes 14a are formed through the end wall 14A. Except for these points, the connecting member 10A is identical in construction to the connecting member 10 of FIG. 3, and therefore explanation thereof is omitted, with identical reference numerals denoting identical portions, respectively.

Figure 5:
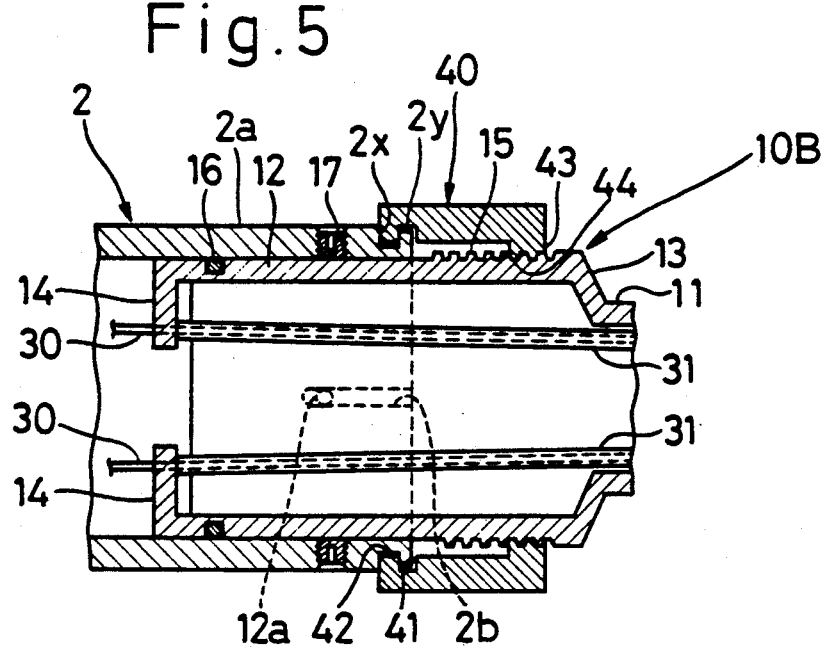
FIGS. 5 and 6 are cross-sectional views showing modified wire tension-adjusting mechanisms, respectively.

FIG. 5 shows a modified form of the invention in which a fine adjustment of the tension of wires 30 can be effected. An annular groove 2x is formed in an outer peripheral surface of a front portion 2a of a body 2 adjacent to the front end of the body 2. As a result, an annular projection 2y extending radially outwardly is formed at the front end of the body 2 immediately adjacent to the annular groove 2x. A connecting member 10B is longer than the connecting member 10 shown in FIG. 2, and has an externally-threaded portion 15 formed on an outer periphery of a rear portion (slide portion) 12 adjacent to a step portion 13. An adjustment ring 40 is mounted on the body 2 and the rear portion 12 of the connecting member 10B. An annular groove 41 is formed in the inner peripheral surface of the adjustment ring 40 adjacent to the rear end thereof. As a result, an annular projection 42 extending radially inwardly is formed at the rear end of the adjustment ring 41 immediately adjacent to the groove 41. An annular projection 43 extending radially inwardly is formed at the front end of the adjustment ring 41, and an internally-threaded portion 44 is formed on the inner periphery of the annular projection 43. The projection 2y of the body 2 is received in the groove 41 of the adjustment ring 40, and the projection 42 of the adjustment ring 40 is received in the groove 2x of the body 2. Therefore, the adjustment ring 40 is angularly movable about its axis relative to the body 2, but is prevented from movement relative to the body 2 in the axial direction. The internally-threaded portion 44 of the adjustment ring 40 is threaded on the externally-threaded portion 15 of the connecting member 10B. When the adjustment ring 40 is angularly moved about its axis, the connecting member 10B is slightly moved relative to the body 2 in the axial direction because of the threaded connection between the threaded portions 15 and 44. Except for the above arrangements, this embodiment is identical in construction to the embodiment of FIG. 2, and therefore explanation thereof is omitted, with identical reference numeral denoting identical portions, respectively.

Figure 6:
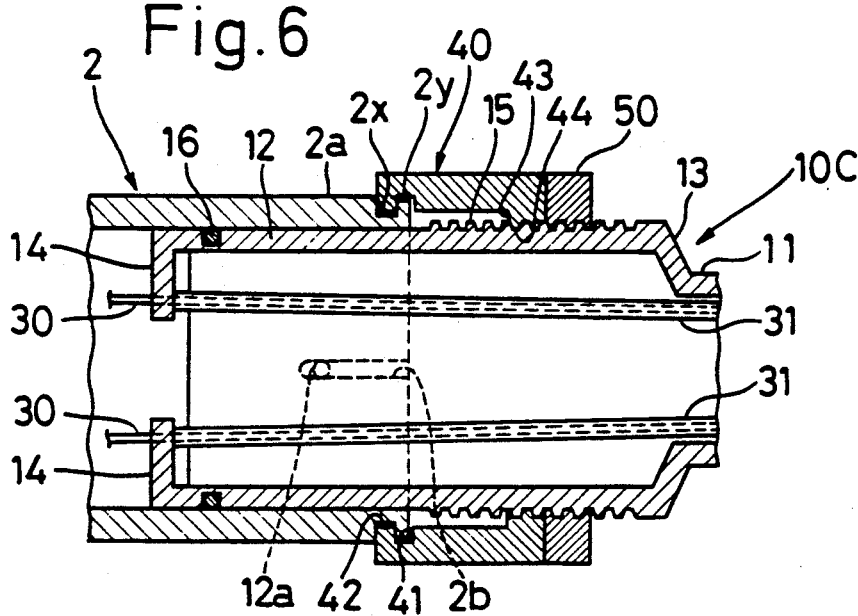

In an embodiment of the invention shown in FIG. 6, a lock nut 50 is threaded on an externally-threaded portion 15 of a connecting member 10C. By threadedly moving the lock nut 50 toward an adjustment ring 40, the rear end face of the adjustment ring 40 is firmly held against a side wall of a groove 2x of a body 2. As a result, the angular movement of the adjustment ring 40 is prohibited, and therefore the axial movement of the connecting member 10C is prohibited.

Figure 7:
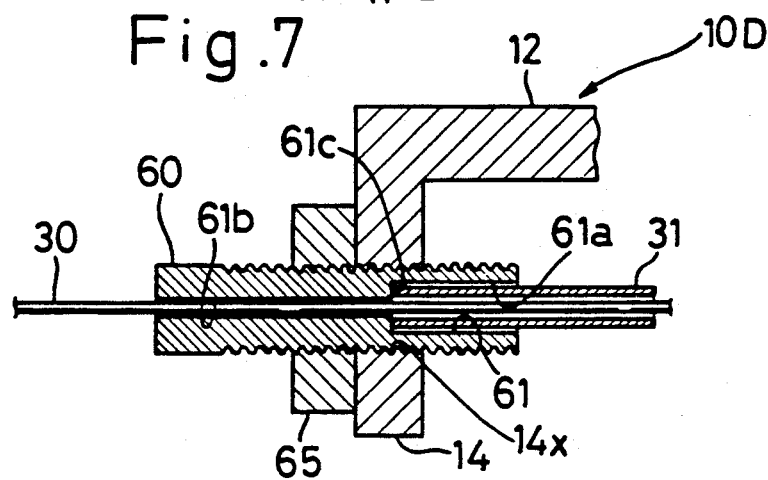
FIG. 7 is a fragmentary cross-sectional view showing a modified mechanism for retaining a rear end of a guide tube.

In an embodiment shown in FIG. 7, a screw hole 14x is formed through each of a pair of end walls 14 (only one of which is shown) formed on a rear end of a connecting member 10D, the screw hole 14x extending in the direction of the axis of the connecting member 10D. A threaded rod 60 is screwed through the screw hole 14x. A stepped through hole 61 is formed axially through the threaded rod 60. A rear end portion of a guide tube 31 is received in a greater-diameter portion 61a of the through hole 61, and a wire 30 is passed through a smaller-diameter portion 61b of the through hole 61. The rear end of the guide tube 31 is retained by a step or shoulder 61c on the inner peripheral surface of the through hole 61. If the length of the guide tube 31 is shorter than a predetermined length, so that there is a play between the rear end of the guide tube 31 and the step 61c, the threaded rod 60 is rotated to be moved in a right direction (FIG. 7). By doing so, the step 61c of the through hole 61 can be abutted against the rear end of the guide tube 31. Also, if the length of the guide tube 31 is longer than the predetermined length, so that the rear end of the guide tube 31 is strongly held against the step 61c of the through hole 61 to thereby cause meandering of the guide tube 31, the threaded rod 60 is rotated to be moved in a left direction (FIG. 7). A lock nut 65 is threaded on the threaded rod 60. In a loosened condition of the lock nut 65, the above adjustment of the position of the threaded rod 65 is carried out. By tightening the lock nut 65, the threaded rod 60 is fixed relative to the end wall 14.

The present invention is not limited to the above embodiments, and various modifications can be made. The number of the wires is not limited to two. For example, when it is intended to bend the bending tube only in one direction, only one wire is used. When four wires are used, a pair of operating mechanisms are needed, and each pair of wires are connected at their rear ends to a respective one of the two operating mechanisms. In this case, preferably, two connecting members are used, and by adjusting the position of each of the connecting members, the tension of the corresponding pair of wires is adjusted. More specifically, the rear portion of the first connecting member is mounted on the front portion (guide portion) of the body for axial sliding movement relative thereto, but against angular movement relative thereto. The rear portion of the second connecting member is mounted on the front portion of the first connecting member for axial sliding movement relative thereto, but against angular movement relative thereto. The rear end portion of the insertion tube is mounted on the front portion of the second connecting member. The rear ends of one pair of guide tubes respectively guiding one pair of wires are retained by retaining means provided at the first connecting member. The rear ends of the other pair of guide tubes respectively guiding the other pair of wires are retained by retaining means provided at the second connecting member. After the position adjustment, the rear portion of the first connecting member is fixed to the body, for example, by fixing screws threaded into the guide portion of the body, as in the embodiment of FIG. 2. The rear portion of the second connecting member is fixed to the first connecting member by fixing screws threaded into the front portion of the first connecting member.

The rear end of each guide tube may be fixedly secured to the rear end portion of the insertion tube by brazing or the like. The angular movement-preventing means constituted by the slot and the pin-like projection may be omitted.

The rear portion (slide portion) of the connecting member may be fitted on the outer periphery of the front portion (guide portion) of the body.

The bending device of the present invention can be applied to the type of endoscope having a rigid insertion tube, and to an electronic endoscope utilizing an image sensor, and also to a surgical catheter. In the case where the insertion tube is rigid, the rear end portion of the insertion tube may be inserted directly into the front portion of the body without the use of the connecting member. In the case where the insertion tube is flexible, the rear end portion of the insertion tube may be filled with a resin, and may be inserted directly into the front portion of the body without the use of the connecting member.

What is claimed is:

1. A bending device comprising:
   (a) a body;
   (b) insertion tube means extending from a front end of said body, a rear end portion of said insertion tube means being supported on a front portion of said body for movement relative to said body along an axis of said insertion tube means;
   (c) fixing means for releaseably fixing the rear end portion of said insertion tube means to the front portion of said body at a desired position within a predetermined range of axial movement of said insertion tube means;
   (d) a bending tube extending from a front end of said insertion tube means;
   (e) operating means mounted on said body in a fixed position for bending said bending tube in a remotely controlled manner;
   (f) a wire passing through said bending tube and said insertion tube means, said wire being connected at one end thereof to a front end of said bending tube and connected at the other end thereof to said operating means so as to transmit an operating force of said operating means to said bending tube, the tension of said wire being determined by the position of the rear end portion of the insertion tube means relative to the body;
   (g) a guide tube guiding said wire therethrough, a front end of said guide tube being secured to a rear end of said bending tube, a rear end of said guide tube being retained by the rear end portion of said insertion tube means; and
   (h) angular movement-preventing means for preventing angular movement of the rear end portion of said insertion tube means relative to said body while allowing axial movement of the rear end portion of said insertion tube means relative to said body.

2. A bending device according to claim 1, in which said fixing means comprises a fixing screw which is threaded through a peripheral wall of the front portion of said body, and is abutted at its distal end against an outer peripheral surface of said rear end portion of said insertion tube means to thereby fix said insertion tube means relative to said body.

3. A bending device according to claim 1, in which said angular movement-preventing means comprises a slot formed in the front portion of said body and extending along the axis of said front portion, and a projection formed on and extending radially outwardly from the outer peripheral surface of the rear end portion of said insertion tube means, said projection being received in said slot for movement therealong.

4. A bending device according to claim 1, further comprising an adjustment ring, a rear portion of said adjustment ring being connected to said front portion of said body in such a manner that said adjustment ring is angularly movable about its axis and is immovable along the axis of said front portion, an internally-threaded portion being formed on an inner periphery of a front portion of said adjustment ring, the rear end portion of said insertion tube means having an externally-threaded portion, said externally-threaded portion being threadedly engaged with said internally-threaded portion, so that upon angular movement of said adjustment ring, said insertion tube means is moved along the axis thereof to adjust its position relative to said body.

5. A bending device according to claim 4, in which said fixing means comprises a lock nut threaded on said externally-threaded portion of said insertion tube means, so that when said lock nut is held against said adjustment ring, the angular movement of said adjustment ring relative to said body is prevented to prevent the axial movement of said insertion tube means relative to said body.

6. A bending device according to claim 1, in which the front portion of said body serves as a tubular guide portion, said insertion tube means comprising an insertion tube and a tubular connecting member, a front portion of said connecting member serving as a mounting portion on which said insertion tube is mounted, a rear portion of said connecting member serving as a slide portion which is slidably supported by said guide portion of said body so as to move along the axis of said guide portion, and said fixing means fixing said slide portion of said connecting member to said guide portion of said body.

7. A bending device according to claim 6, in which the rear end of said guide tube is retained by said connecting member.

8. A bending device according to claim 7, in which said connecting member has a wall extending radially inwardly from a peripheral wall thereof, said wall serving as retaining means for retaining the rear end of said guide tube, and said wall having a through hole through which said wire is passed.

9. A bending device according to claim 7, in which said connecting member has a wall extending radially inwardly from a peripheral wall thereof, a threaded rod being threaded through said wall, said threaded rod having a stepped through hole extending axially therethrough, said stepped through hole having a greater-diameter portion, a smaller-diameter portion and a step portion interconnecting said greater-diameter portion and said smaller-diameter portion, said guide tube being inserted in said greater-diameter portion of said through hole and abutted at its rear end against said stepped portion, and said wire being passed through said smaller-diameter portion of said through hole.

10. A bending device comprising:
 (a) a body;
 (b) insertion tube means extending from a front end of said body, a rear end portion of said insertion tube means being supported on a front portion of said body for movement relative to said body along a axis of said insertion tube means;
 (c) fixing means for releaseably fixing the rear end portion of said insertion tube means to the front portion of said body at a desired position within a predetermined range of axial movement of said insertion tube means;
 (d) a bending tube extending from a front end of said insertion tube means;
 (e) operating means mounted on said body in a fixed position for bending said bending tube in a remotely controlled manner;
 (f) a wire passing through said bending tube and said insertion tube means, said wire being connected at one end thereof to a front end of said bending tube and connected at the other end thereof to said operating means so as to transmit an operating force of said operating means to said bending tube;
 (g) a guide tube guiding said wire therethrough, a front end of said guide tube being secured to a rear end of said bending tube, a rear end of said guide tube being retained by the rear end portion of said insertion tube means; and
 (h) an adjustment ring, a rear portion of said adjustment ring being connected to said front portion of said body in such a manner that said adjustment ring is angularly movable about its axis and is immovable along the axis of said front portion, an internally-threaded portion being formed on an inner periphery of a front poriton of said adjustment ring, the rear end portion of said insertion tube means having an externally-threaded portion, and said externally-threaded portion being threadedly engaged with said internally threaded portion, so that upon angular movement of said adjustment ring, said insertion tube means is moved along the axis thereof to adjust its position relative to said body and said operating means, the tension of said wire being determined by the position of the rear end portion of said insertion tube means relative to said body and said operating means.

* * * * *